(12) United States Patent
Huang et al.

(10) Patent No.: US 8,802,443 B2
(45) Date of Patent: Aug. 12, 2014

(54) METHOD FOR IDENTIFYING GAMBIERED GUANGDONG SILK

(71) Applicant: Shenzhen Liangzi Fashion Industrial Co., Ltd., Guangdong (CN)

(72) Inventors: Zhihua Huang, Guangdong (CN); Xueming Liu, Guangdong (CN); Hongying Zhou, Guangdong (CN); Yingying Wu, Guangdong (CN)

(73) Assignee: Shenzhen Liangzi Fashion Industrial Co., Ltd., Shenzhen (CN)

( * ) Notice: Subject to any disclaimer, the term of this patent is extended or adjusted under 35 U.S.C. 154(b) by 0 days.

(21) Appl. No.: 14/013,071

(22) Filed: Aug. 29, 2013

(65) Prior Publication Data
US 2014/0073056 A1  Mar. 13, 2014

(30) Foreign Application Priority Data
Sep. 7, 2012  (CN) .......................... 2012 1 0330269

(51) Int. Cl.
*G01N 33/68* (2006.01)
*G01N 30/02* (2006.01)

(52) U.S. Cl.
CPC ..................................... *G01N 33/68* (2013.01)
USPC ............. 436/86; 436/106; 436/155; 436/161; 436/164; 436/174; 436/183

(58) Field of Classification Search
USPC ............. 436/80, 86, 106, 119, 155, 161, 164, 436/174, 178, 183; 422/68.1, 70, 78, 89; 210/656
See application file for complete search history.

*Primary Examiner* — Maureen Wallenhorst

(57) ABSTRACT

A method for identifying gambiered Guangdong silk includes the steps of: detecting the surface state of fiber by microscope; detecting the pyrolysis fragments of fabrics by pyrolysis gas chromatography; determining the crude protein content in the fiber by Kjeldahl determination; and detecting the dye component of the fabrics by high performance liquid chromatography. The method of the present invention can accurately identify the true and fake, good and bad of the gambiered Guangdong silk, and then make an accurate evaluation on the gambiered Guangdong silk; and the present invention is simple, useful, environmental and has low cost.

3 Claims, 5 Drawing Sheets

METHOD FOR IDENTIFYING GAMBIERED GUANGDONG SILK

CROSS-REFERENCE TO RELATED APPLICATIONS

This present invention claims the benefit of Chinese Patent Application No. CN201210330269.7, filed on Sep. 7, 2012; the contents of which are hereby incorporated by reference.

FIELD OF THE INVENTION

The present invention relates to an identification method, and more particularly to a method for identifying the quality of gambiered Guangdong silk by Kjeldahl determination, High Performance Liquid Chromatography (HPLC) and Pyrolysis Gas Chromatography (PGC).

BACKGROUND OF THE INVENTION

With the development of science and technology and the improvement of people's living standard, customers demand much higher on green and environmental protection of the clothing. The contemporary people require that the clothing must be comfortable, healthy and beautiful. The gambiered Guangdong silk (gambiered Guangdong gauze) is commonly known as gambiered Canton gauze or gambiered Canton silk, which is the famous traditional product of Guangdong silk products and one of the pure silk fabrics dyed by pure vegetable dye. The gambiered Guangdong silk is totally handmade, it needs more than ten steps and more than ten days to finish. Its manufacturing process includes the steps of: weaving white body silk from mulberry silk; dip-dying the white body silk by using dye yam juice; spreading the dip-dyed white body silk on the grass before sunrise; and spreading the Guangdong local unique non-polluting pond sludge on the silk surface. By the transpiration of dew, the dye yam juice and pond sludge are interpenetrated with each other, then the gambiered Guangdong silk gradually presents shiny luster. The clothes made of gambiered Guangdong silk are durable and easy to wash, light and cool, smooth and soft, and especially suitable for wearing in hot summer days. With the increase of the market share and recognition of the products made of gambiered Guangdong silk, there unavoidably has some fake gambiered Guangdong silks on the market, however, no any method is provided for accurately identifying the true and fake, good and bad of the gambiered Guangdong silk.

SUMMARY OF THE INVENTION

An object of the present invention is to provide a method for accurately identifying the quality of the gambiered Guangdong silk, so as to overcome the existing problems. To achieve above object, the present invention adopts the following technical solution:

A method for identifying gambiered Guangdong silk, including the steps of:

(1) detecting by microscope: putting a section of fiber bundle of detected fabric at the center of a glass slide, dropping a drop of 75% ethanol and covering with a cover slip, and then observing the surface state of the fibers under a microscope;

carrying on the next step of detection if on the fibers or between the fibers has black brown particles with particle size greater than the fiber diameter; otherwise it can be concluded that the detected fabric is not gambiered Guangdong silk and the detection is ended;

(2) detecting by pyrolysis gas chromatography: forming a finger-print chromatogram based on the data obtained by analyzing the fibers by pyrolysis gas chromatography; wherein the pyrolysis temperature is 450° C. and the pyrolysis time is 25~35 s, preferably is 30 s;

carrying on the next step of detection if the correlation between the finger-print chromatogram of the fiber and that of the standard gambiered Guangdong silk reaches more than 90%; otherwise it can be concluded that the detected fabric is not gambiered Guangdong silk and the detection is ended;

(3) detecting by high performance liquid chromatography: soaking appropriate fibers in acetone solution and carrying on an extraction, and then analyzing the compositions of the extracting solution by high performance liquid chromatography; wherein the chromatographic column is XDB-C18 or SB-C18, the wavelength is 280 nm, the mobile phase is the mixed liquor of acetonitrile and 0.4% acetic acid, and the volume ratio of acetonitrile to 0.4% acetic acid is 1:99;

if the finger-print chromatogram of the extracting solution of the fibers has seven common peaks which approximately appear at 8.4 min, 12.4 min, 15.8 min, 18.2 min, 22.1 min, 24.1 min and 26.6 min, it can be concluded that the detected fabric is gambiered Guangdong silk and the next step of detection can be carried on to make an accurate judgment; otherwise it can be concluded that the detected fabric is not gambiered Guangdong silk; and (4) detecting by Kjeldahl determination, reacting appropriate fibers with copper sulfate, potassium sulfate and sulfuric acid, converting the organic nitrogen in the fibers into inorganic ammonium salt and then converting the inorganic ammonium into nitrogen under alkaline condition, and calculating the crude protein content of the fibers according to the content of nitrogen;

if the crude protein content of the fiber is more than 74% and less than 90%, it can be accurately concluded that the detected fabric is gambiered Guangdong silk.

Compared with the prior art, the beneficial effects of the present invention include: the method of the present invention can accurately identify the true and fake, good and bad of the gambiered Guangdong silk, and then make an accurate evaluation on the gambiered Guangdong silk; and the present invention is simple, useful, environmental and has low cost.

DETAILED DESCRIPTION OF ILLUSTRATED EMBODIMENTS

The following illustration combining the accompanying drawings and embodiments will facilitate a clear understanding of the object, technical solution and advantages of the present invention for an ordinary person skilled in the art.

In an embodiment, take thirty kinds of fabric samples (as shown in Table 1) as example to be detected and then compare the detected data, thereby building standard detected data of the gambiered Guangdong silk.

TABLE 1

| NO. | SAMPLES |
|---|---|
| 1 | Inferior gambiered Guangdong silk |
| 2 | Traditional gambiered Guangdong silk 060728 |
| 3 | Traditional gambiered Guangdong silk 060624 |
| 4 | Traditional gambiered Guangdong silk 060901 |
| 5 | Traditional gambiered Guangdong silk 061013 |
| 6 | Traditional gambiered Guangdong silk 070810 |
| 7 | Traditional gambiered Guangdong silk 070710 |
| 8 | Traditional gambiered Guangdong silk 071110 |
| 9 | Traditional gambiered Guangdong silk 071010 |
| 10 | Traditional gambiered Guangdong silk 080415 |
| 11 | Traditional gambiered Guangdong silk 080320 |
| 12 | Traditional gambiered Guangdong silk 080513 |
| 13 | Traditional gambiered Guangdong silk 071213 |
| 14 | Fake gambiered Guangdong silk with coating (Green) |
| 15 | Gray fabric of gambiered Guangdong silk 11160 |
| 16 | Traditional gambiered Guangdong silk treated by washing |
| 17 | Rubberized fabric |
| 18 | Ramie cotton slub yarn |
| 19 | Matt chemical fiber (Red) |
| 20 | Twill |
| 21 | Linen (Green) |
| 22 | Habotai (Black) |
| 23 | Fake gambiered Guangdong silk with coating (Red) |
| 24 | Fake gambiered Guangdong silk (Rayon) |
| 25 | Colored gambiered Guangdong silk (Blue-green) |
| 26 | Colored gambiered Guangdong silk (Rose-red) |
| 27 | Colored gambiered Guangdong silk (Blue) |
| 28 | Colored gambiered Guangdong silk (Red) |
| 29 | Colored gambiered Guangdong silk (Purple) |
| 30 | Colored gambiered Guangdong silk (Green) |

Step 1: observing the surface state of the fiber under a microscope.

Figure 1:
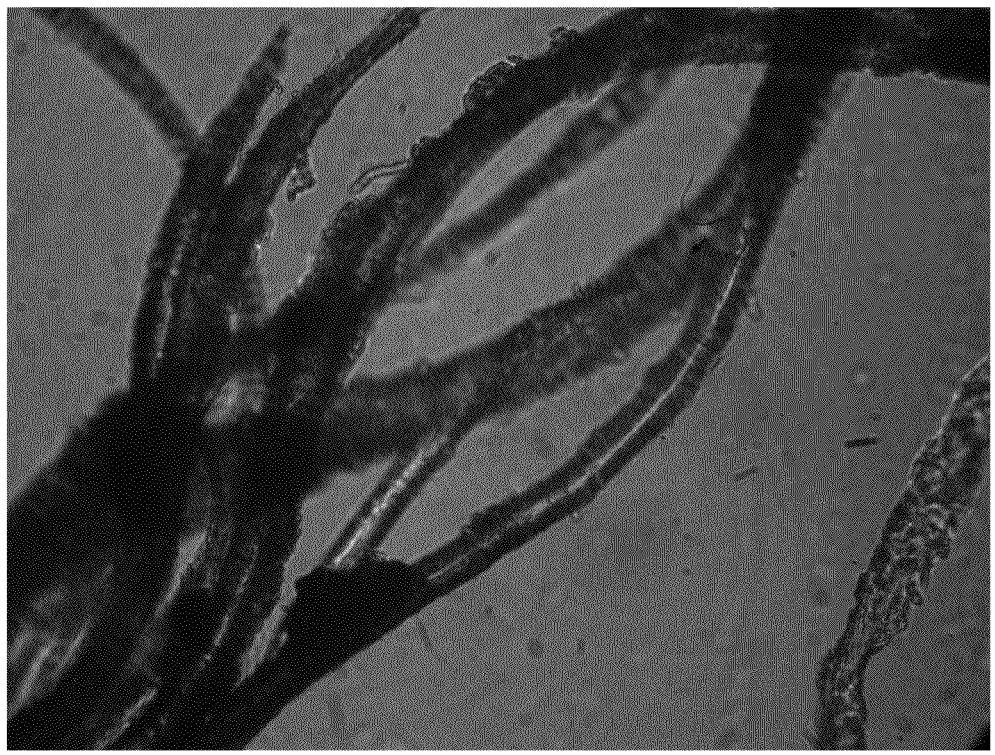
FIG. 1 is a fiber micrograph of the NO. 2 sample.
Figure 2:
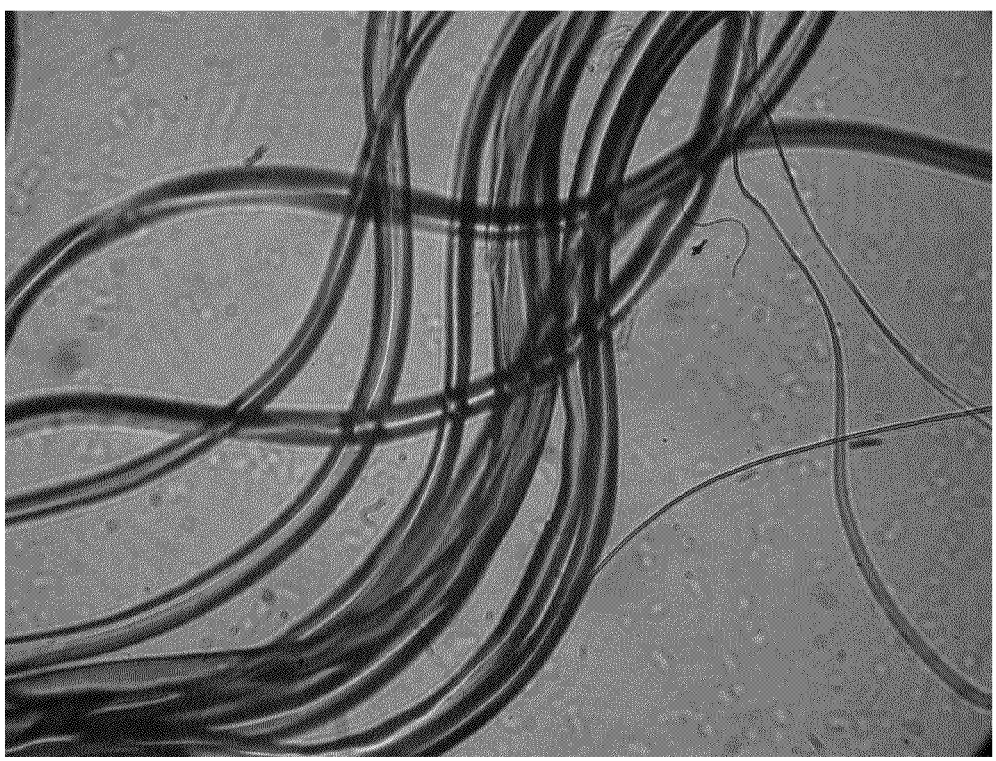
FIG. 2 is a fiber micrograph of the NO. 22 sample.

Use a microscope to respectively observe the fabric samples listed on the Table 1. Firstly, cut out a section of fiber bundle; use a pin to break it up (untwisting); then put it at the center of a glass slide by using tweezers; drop a drop of 75% ethanol onto it and cover it with a cover slip (do not leave bubble); put the glass slide onto the objective stage of the microscope; regulate the ocular lens (WF16×14) and the objective lens (×40) of the microscope until the view is clear enough; regulate the position of the glass slide until the target object is located at the center of the view; and finally record the observed result. The fabric samples of NO. 1~13, NO. 16 and NO. 24~30 are all have been treated by the manufacturing process of gambiered Guangdong silk, thus, on the fabric fibers or between the fibers, there has some black brown particles with particle size greater than the fiber diameter, as shown in the fiber micrograph of the NO. 2 sample (FIG. 1). The fabric samples, which have not been treated by the manufacturing process of gambiered Guangdong silk, have uniform dyeing, thus, on these fabric fibers or between the fibers, there has no black brown particle with particle size greater than the fiber diameter, as shown in the fiber micrograph of the NO. 22 sample (FIG. 2). The complexing dyes between the fibers of the NO. 1 sample are less than the samples of NO. 2~13, it may be because of its poor color fastness and then easy to be eluted. The fibers of the NO. 1 sample are coarser than that of the samples of NO. 2~13. Between the fibers of the NO. 25~30 samples, there has less black brown particle than the traditional gambiered Guangdong silk, it may be because of much dye yam complex being eluted by sand washing. In view of the above detected result, we can distinguish the fake and shoddy products from the superior gambiered Guangdong silks.

Step 2: detecting the pyrolysis fragments of the fabrics by pyrolysis gas chromatography.

Respectively detect the samples under different pyrolysis temperature and different pyrolysis time. The experimental result shows: when the temperature is below 450° C., the samples can not be pyrolyzed completely, and when the temperature is above 450° C., the samples have less peaks, bad repeatability and some peaks have been decomposed, thus the temperature of 450° C. is a suitable pyrolysis temperature. When the pyrolysis time is less than 25 s, there has less peaks; and when the pyrolysis time is more than 35 s, the number of peaks decreases, some peak types have been changed, and some inseparable twin peaks appear, it may be because the pyrolysis time is too long to cause a second-order reaction. When the pyrolysis time is 30 s, the number of peaks is appropriate, thus, 30 s is an appropriate pyrolysis time.

Apparatus includes: GC-16A gas chromatograph, hydrogen flame detector (FID), PRY-2R pyrolysis device; chromatographic column is: 30 m*0.32 mmXC-1701 quartz capillary column; detector temperature is: $T_D=250°$ C.; injector temperature is: $T_J=230°$ C.; column temperature is:

$$T_{C.} = 60° \text{ C. (3 min)} \xrightarrow{4° \text{ C./min}} 230° \text{ C. (20 min)};$$

pyrolysis temperature is: $T_P=450°$ C.; pyrolysis time is: t=30 s; injection volume is: 5 mg.

Respectively take 10 g of each fabric sample to be cut into pieces for standby application.

Figure 5:
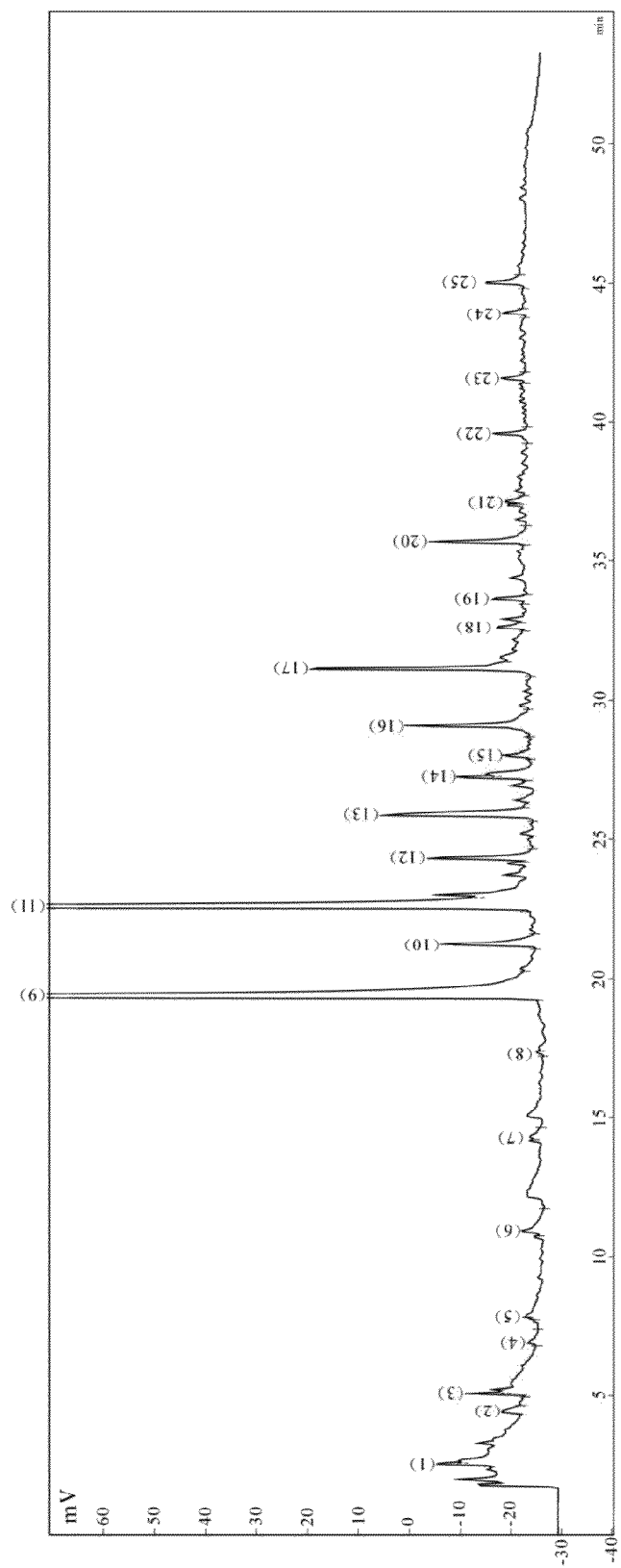
FIG. 5 is a pyrolysis gas chromatogram of the NO. 7 sample.
Figure 6:
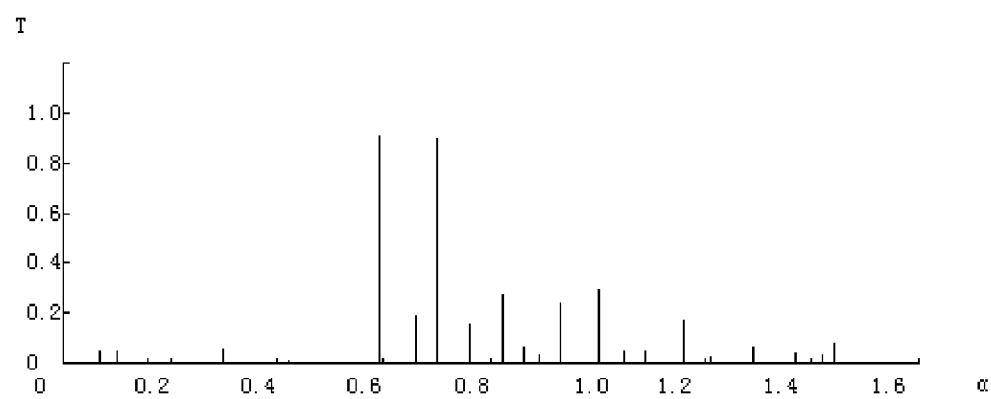
FIG. 6 is a finger-print chromatogram of the NO. 7 sample.

The detected result shows that each of various gambiered Guangdong silk samples has about 35 pyrolysis peaks, wherein more than 90% are common peaks, as shown in FIG. 5 which is a pyrolysis gas chromatogram of the NO. 7 sample. Compare the common peaks which can meet the condition of Kr>1% (wherein Kr is the ratio of the peak area of each component and the total area of all the common peaks), take the peak of NO. 20 as reference (its peak value is stable and its a is set to be 1), and then determine the values of a and T of each component to produce the finger-print chromatogram of each sample, as shown in FIG. 6, which is a finger-print chromatogram of the NO. 7 sample (wherein a is the ratio of the adjusted retention value of each component and the adjusted retention value of the reference peaks; T=1 g(Sr+1), Sr is the ratio of the peak area of each component and the peak area of the reference peak). By observing and analyzing the finger-print chromatograms, it can been seen that the finger-print chromatograms of the samples of NO. 1~13, NO. 15~16 and NO. 22 are roughly the same, they have the same number of common peaks, but their peak values have certain difference. From clustering analysis of the finger-print chromatograms, it can been seen that the samples of NO. 1~13, NO. 15~16 and NO. 22 have high correlation, even exceeding 90%, thus they can be classified as the same class.

Based on the above analysis by pyrolysis gas chromatography, if the correlation between the finger-print chromatogram of the fabric sample and that of the standard gambiered Guangdong silk reaches more than 90%, we can identify the fake products which use not real silk materials.

Step 3: detecting the dye compositions of the fabrics by high performance liquid chromatography.

Chromatographic column is: XDB-C18 or SB-C18, 250 mm*1.5 um; column temperature is: 30° C.; wavelength is: 280 nm; mobile phase is: acetonitrile/0.4% acetic acid (V/V=1/99); acquisition time is: 50 min.

Respectively soak 0.7 g of each different sample in acetone solution and carry on an ultrasonic extraction for 20 min, filter the extracting solution and then carry on a concentration under reduced pressure; add some methanol into the concentrated solution to produce 1 ml mixed solution; and then use a 0.45 um millipore filter to filter the mixed solution; finally test the filtered solution on a machine.

Figure 3:
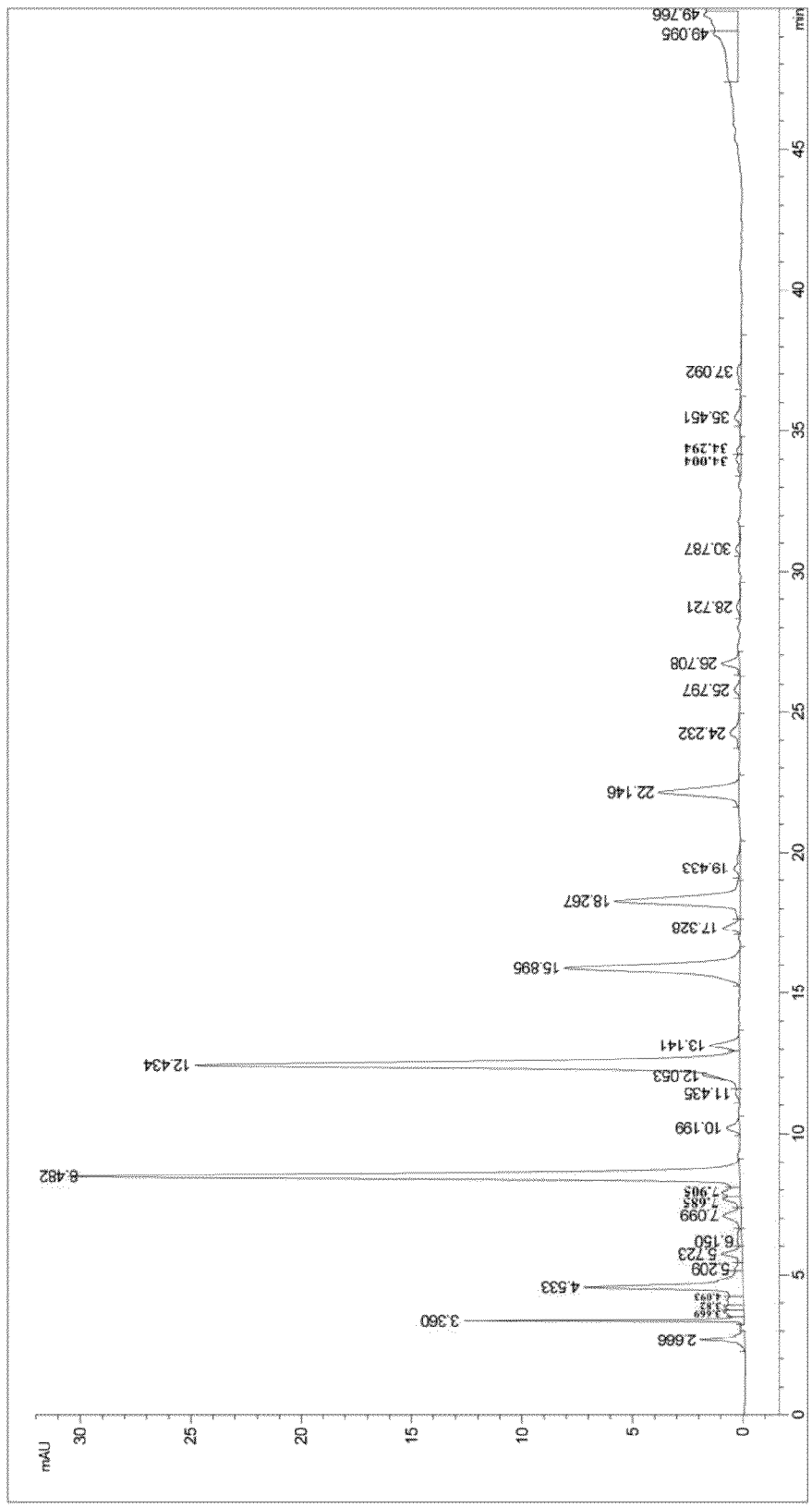
FIG. 3 is a high performance liquid chromatogram of the NO. 2 sample.
Figure 4:
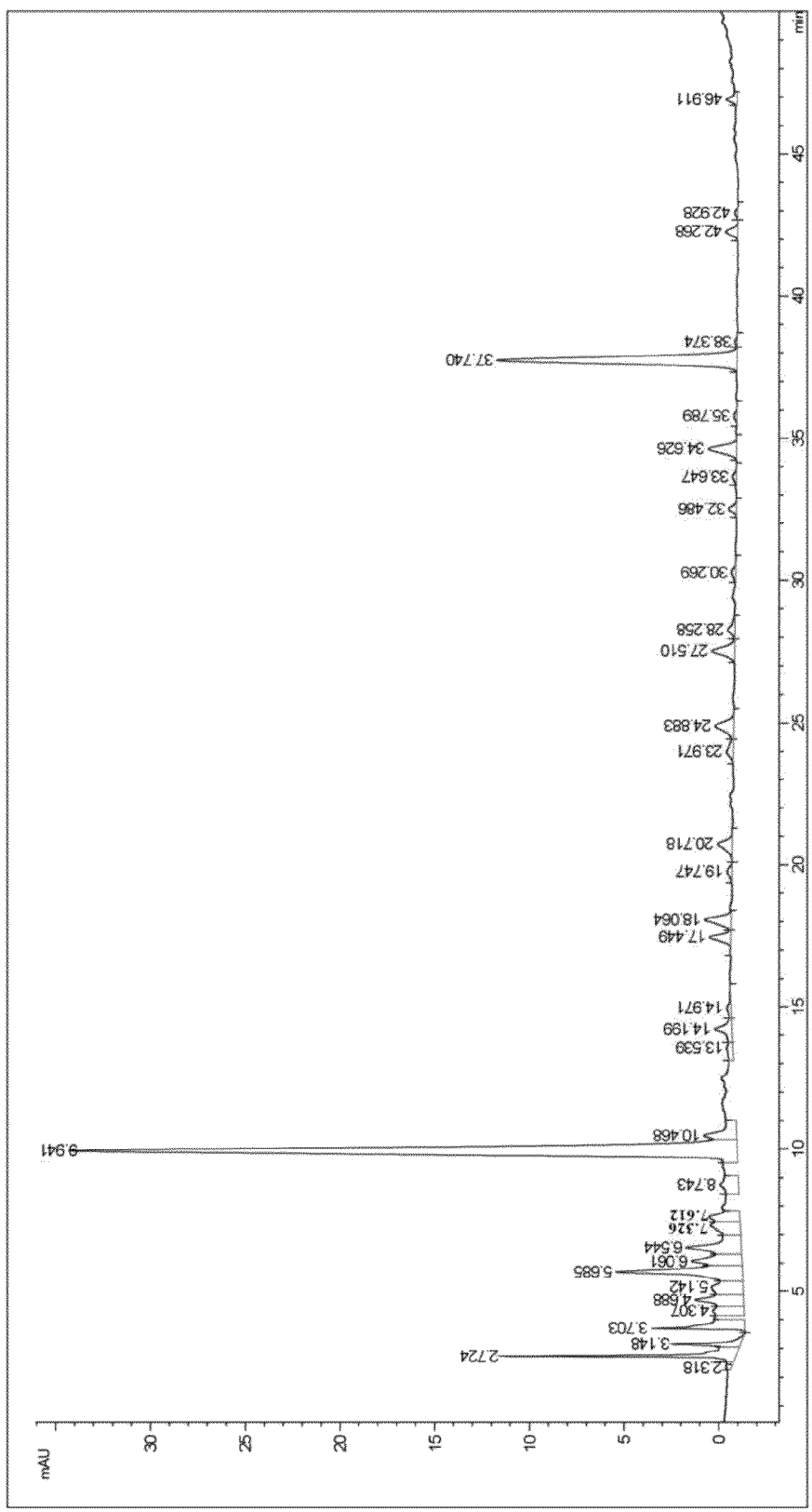
FIG. 4 is a high performance liquid chromatogram of the NO. 26 sample.

The detected result shows that the peak type and peak shape of the samples of the traditional gambiered Guangdong silk (samples of NO. 2~13 and NO. 16) are roughly the same, as shown in the high performance liquid chromatogram of the NO. 22 sample (FIG. 3). The peaks appear at 8.450 min (the first common peak), 12.384 min (the second common peak), 15.814 min (the third common peak), 18.203 min (the fourth common peak), 22.063 min (the fifth common peak), 24.118 min (the sixth common peak) and 26.600 min (the seventh common peak) are common peaks of the fabric samples of the gambiered Guangdong silk. Detect the NO. 2 sample eight times repeatedly and then calculate the standard deviation of each representative peak, as shown in the following Table 2. The standard deviation of appearing time of the seven common peaks is less than or equal to 0.7382. It has certain reference significance to statistics and its experiment repeatability is very good. As sampling time goes on, the appearing time of the common peaks will be slightly changed (mostly delayed), but its moving range is very narrow, within allowable error. Because the common peaks have relatively large peak value, they are far away from each other and have obvious differences from the adjacent small peaks, the tiny time lapse will not affect analysis and judgment. By comparing the test sample with the standard sample, we can conclude that the fourth common peak, six common peak and seventh common peak are clove acid, benzoic acid and ferulic acid, respectively. The peak type of the common peak of the NO. 1 sample has large change, it may be because of the poor color fastness of the NO. 1 sample, dye yarn complexing on the sample being eluted during washing and different components having different elution results. The dyeing process of the NO. 24 sample is the same as that of the NO. 2~13 samples, thus the peak type and peak shape of its chromatogram are basically the same as that of the NO. 2~13 samples. However, the fabric samples which are treated by other dying processes have very different high performance liquid chromatogram from the fabric samples of gambiered Guangdong silk, thus the fabric samples of gambiered Guangdong silk can be identified directly by comparing the chromatograms. The high performance liquid chromatograms of the colored gambiered Guangdong silk samples have fifteen common peaks, seven of which are the same as that of the traditional gambiered Guangdong silk. Taking the chromatogram of the rose-colored gambiered Guangdong silk as example (shown in FIG. 4), the appearing times of other eight common peaks are 10.468 min, 14.199 min, 20.718 min, 33.647 min, 34.626 min, 37.740 min, 42.268 min and 46.911 min, respectively. During the manufacturing process of the colored gambiered Guangdong silk, part of dye yarn will be eluted by sand washing, thus the peak shapes of their common peaks, which are even hard to detect, are smaller than that of the traditional gambiered Guangdong silk.

It can been seen from above analysis, the fabrics, which are treated by the manufacturing process of the traditional gambiered Guangdong silk, will retain the chemical components of dye yarn, and the high performance liquid chromatograms obtained by high performance liquid chromatography have the same common peaks with similar peak type and peak shape. By using this detecting method, the fake products, which use printing to copy the marks of the gambiered Guangdong silk without dye yarn dyeing, can be identified.

TABLE 2

| Times | NO. | | | | | | |
|---|---|---|---|---|---|---|---|
| | 1 | 2 | 3 | 4 | 5 | 6 | 7 |
| 1 | 8.450 | 12.384 | 15.814 | 18.203 | 22.063 | 24.118 | 26.600 |
| 2 | 8.482 | 12.434 | 15.895 | 18.267 | 22.146 | 24.232 | 26.708 |
| 3 | 8.525 | 12.512 | 15.994 | 18.369 | 22.267 | 24.397 | 26.881 |
| 4 | 9.099 | 13.248 | 16.957 | 19.226 | 23.307 | 25.626 | 28.132 |
| 5 | 9.117 | 13.266 | 16.976 | 19.246 | 23.325 | 25.641 | 28.147 |
| 6 | 9.125 | 13.278 | 16.990 | 19.260 | 23.336 | 25.645 | 28.157 |
| 7 | 9.127 | 13.274 | 16.984 | 19.256 | 23.334 | 25.645 | 28.154 |
| 8 | 9.126 | 13.278 | 16.988 | 19.261 | 23.330 | 25.636 | 28.152 |
| Standard Deviation | 0.3284 | 0.4287 | 0.5601 | 0.5042 | 0.6069 | 0.7231 | 0.7382 |

Step 4: determining the crude protein content in the fiber by Kjeldahl determination.

Weight out 0.5 g of the fabric sample, put it into a flask, and add 0.5 g of copper sulfate ($CuSO_4$), 5 g of potassium sulfate ($K_2SO_4$) and 20 ml of concentrated sulfuric acid ($H_2SO_4$), mix the mixture thoroughly, heat the mixture carefully until all of the carbonized foams of the mixture completely disappear and then enhance the firepower, keep the liquid in the flask micro-boiling until the liquid is transparent blue-green, and continues heating for 30 min, and then take it down to cool, finally add appropriate rimming agent (pumice stone). Add 50 ml of 2% boric acid solution and 5 drops of bromo-cresol green (this mixed indicator is red in acidic condition, gray in neutral condition, green in alkaline condition) into a 250 ml triangular flask, connect to a distilling apparatus, insert a condenser pipe under the boric acid solution. Add 40% sodium hydroxide (NaOH), mix and then heat the mixture until completely distill amidogen (NH2), collect about 150 ml steams within 30 min, move the condenser pipe away from the liquid level and then continue distilling for 1 min, and use a few distilled water to wash the external of the outflow end of the condenser pipe. Take the triangular flask down, use 0.1M hydrogen chloride (HCl) to titrate the solution in the triangular flask until gray disappears, and then record the volume of the consumed hydrogen chloride (HCl).

At the same time, carry on a blank experiment.

The calculation formula of the nitrogen content of the fabric samples is:

$$X = \frac{(V1 - V2) \times N \times 0.014}{M} \times F \times 100$$

The crude protein content of the fabric samples is equal to 6.25×

Wherein, V1 is: the volume of the consumed hydrochloric acid; V2 is: the volume of the consumed hydrochloric acid in the blank experiment; N is: the concentration of the hydrochloric acid; M is: the mass of the sample.

Test each fabric sample three times repeatedly to obtain the average of the crude protein content of each fabric sample, as shown in the following Table 3. The crude protein content of the traditional gambiered Guangdong silk (NO. 2~13) is stable within a range of 74.52%~80.75%. The crude protein content of the colored gambiered Guangdong silk (NO. 2~13) is stable within a range of 79.55%~87.05%. Because the colored gambiered Guangdong silk is produced by the steps of sand washing part of river mud and dye yam juice complex and then carrying on a chemical dye, the absolute content of the dye yam juice complex in the whole fabric will reduce, and compared with the traditional gambiered Guangdong silk, the crude protein content will increase. And the crude protein content of the NO. 2 sample (inferior gambiered Guangdong silk) is 102.84%, it may be because during the manufacturing process, the NO. 1 sample has comparatively less complexing dye on the material and has poor color fastness, thus, compared with the high quality gambiered Guangdong silk, the crude protein content in the gray fabric increase. Based on this reason, we can identify the poor quality gambiered Guangdong silk, which uses real silk as gray fabric and is dyed by dye yam dyeing but cutting corners in production. Thus, we can conclude that the crude protein content within a proportional range of 70%-90% must be gambiered Guangdong silk.

TABLE 3

| NO. | Crude Protein Content (%) |
|---|---|
| 1 | 102.84 |
| 2 | 79.02 |
| 3 | 80.51 |
| 4 | 80.75 |
| 5 | 79.27 |
| 6 | 78.76 |
| 7 | 74.91 |
| 8 | 78.07 |
| 9 | 79.43 |
| 10 | 75.35 |
| 11 | 74.52 |
| 12 | 75.48 |
| 13 | 79.14 |
| 14 | 3.89 |
| 15 | 114.34 |
| 16 | 79.22 |
| 17 | 0.56 |
| 18 | 1.98 |
| 19 | 1.12 |
| 20 | 0.75 |
| 21 | 0.80 |
| 22 | 110.31 |
| 23 | 3.98 |
| 24 | 24.90 |
| 25 | 85.57 |
| 26 | 87.05 |
| 27 | 81.85 |
| 28 | 83.71 |
| 29 | 79.55 |
| 30 | 81.98 |

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A method for identifying gambiered Guangdong silk, comprising the steps of:
   (1) detecting by microscope: putting a section of fiber bundle of detected fabric at the center of a glass slide, dropping a drop of 75% ethanol onto the detected fabric and covering with a cover slip, and then observing surface state of the fibers under a microscope;
   carrying on the next step of detection if on the fibers or between the fibers has black brown particles with particle size greater than fiber diameter; otherwise it can be concluded that the detected fabric is not gambiered Guangdong silk and the detection is ended;
   (2) detecting by pyrolysis gas chromatography: forming a finger-print chromatogram based on data obtained by analyzing the fibers by pyrolysis gas chromatography;
   carrying on the next step of detection if a correlation between the finger-print chromatogram of the fiber and that of a standard gambiered Guangdong silk reaches more than 90%; otherwise it can be concluded that the detected fabric is not gambiered Guangdong silk and the detection is ended;
   (3) detecting by high performance liquid chromatography: soaking appropriate fibers in acetone solution and carrying on an extraction, and then analyzing compositions of the extracting solution by high performance liquid chromatography;
   if a finger-print chromatogram of the extracting solution of the fibers has seven common peaks which approximately appear at 8.4 min, 12.4 min, 15.8 min, 18.2 min, 22.1 min, 24.1 min and 26.6 min, it can be concluded that the detected fabric is gambiered Guangdong silk and the next step of detection can be carried on to make an accurate judgment; otherwise it can be concluded that the detected fabric is not gambiered Guangdong silk; and
   (4) detecting by Kjeldahl determination, reacting appropriate fibers with copper sulfate, potassium sulfate and sulfuric acid, converting organic nitrogen in the fibers into inorganic ammonium salt and then converting the inorganic ammonium into nitrogen under alkaline condition, and calculating a crude protein content of the fibers according to the content of nitrogen;
   if the crude protein content of the fiber is more than 74% and less than 90%, it can be accurately concluded that the detected fabric is gambiered Guangdong silk.

2. The method as claimed in claim 1, wherein in the step of detecting by high performance liquid chromatography, chromatographic column is XDB-C18 or SB-C18, wavelength is 280 nm, mobile phase is a mixed liquor of acetonitrile and 0.4% acetic acid which is measured in terms of percentage by volume, and volume ratio of acetonitrile to 0.4% acetic acid is 1:99.

3. The method as claimed in claim 1, wherein in the step of detecting by pyrolysis gas chromatography, pyrolysis temperature is 450° C. and pyrolysis time is 25~35 s.

* * * * *